(12) United States Patent
Woellner Duarte Pereira et al.

(10) Patent No.: US 12,296,529 B2
(45) Date of Patent: May 13, 2025

(54) MODULAR PRINT BED FOR 3D BIOPRINTER

(71) Applicant: 3D SYSTEMS, INC., Rock Hill, SC (US)

(72) Inventors: Taciana Leticia Woellner Duarte Pereira, Philadelphia, PA (US); Thomas Castner, Philadelphia, PA (US); Madeline Winter, Newton Square, PA (US); Ricardo Solorzano, Philadelphia, PA (US)

(73) Assignee: 3D SYSTEMS, INC.

(*) Notice: Subject to any disclaimer, the term of this patent is extended or adjusted under 35 U.S.C. 154(b) by 0 days.

(21) Appl. No.: 17/341,872

(22) Filed: Jun. 8, 2021

(65) Prior Publication Data

US 2021/0379815 A1    Dec. 9, 2021

Related U.S. Application Data

(60) Provisional application No. 63/036,546, filed on Jun. 9, 2020.

(51) Int. Cl.
| | |
|---|---|
| *B29C 64/00* | (2017.01) |
| *B29C 64/112* | (2017.01) |
| *B29C 64/209* | (2017.01) |
| *B29C 64/245* | (2017.01) |
| *B29C 64/255* | (2017.01) |
| *B29C 64/264* | (2017.01) |
| *B29C 64/386* | (2017.01) |

(Continued)

(52) U.S. Cl.
CPC .......... *B29C 64/112* (2017.08); *B29C 64/209* (2017.08); *B29C 64/245* (2017.08); *B29C 64/255* (2017.08); *B29C 64/264* (2017.08); *B29C 64/386* (2017.08); *B33Y 10/00* (2014.12); *B33Y 30/00* (2014.12); *B33Y 50/00* (2014.12)

(58) Field of Classification Search
CPC ...................................................... B29C 64/00
See application file for complete search history.

(56) References Cited

U.S. PATENT DOCUMENTS

| 2015/0037445 A1 | 2/2015 | Murphy et al. |
| 2015/0314613 A1 | 11/2015 | Murphy et al. |

(Continued)

OTHER PUBLICATIONS

Chouhdhry et al, "The arrival of commercial bioprinters—Toward 3D bioprinting revolution!", Int J Bioprint, vol. 4, No. 2, 21 pages, Jun. 17, 2018.

(Continued)

*Primary Examiner* — Matthew J Daniels
*Assistant Examiner* — John W Hatch
(74) *Attorney, Agent, or Firm* — DLA Piper LLP US

(57) ABSTRACT

Disclosed are systems and methods for a bioprinter capable of printing an object having biological components. In some embodiments, the bioprinter includes a modular print bed having a recessed area configured to receive a variable insert and a printer head positioned above the modular print bed. In some embodiments, the printer head has a cartridge for receiving and holding a biomaterial, and an extruder configured to extrude biomaterials from the cartridge onto a portion of the variable insert. The variable insert may include functional elements (e.g., heating, cooling, photo-curing) and/or receiving elements (e.g., well plates).

12 Claims, 4 Drawing Sheets

(51) Int. Cl.
*B33Y 10/00* (2015.01)
*B33Y 30/00* (2015.01)
*B33Y 50/00* (2015.01)

(56) References Cited

U.S. PATENT DOCUMENTS

| | | |
|---|---|---|
| 2016/0263831 A1* | 9/2016 | Li .................... B33Y 30/00 |
| 2017/0066873 A1* | 3/2017 | Gardet ............. B33Y 10/00 |
| 2017/0198252 A1 | 7/2017 | Mironov et al. |
| 2017/0199507 A1 | 7/2017 | Murphy et al. |
| 2017/0369827 A1 | 12/2017 | Langenfeld et al. |
| 2018/0281280 A1* | 10/2018 | Solorzano ............ C12N 5/0062 |
| 2020/0056147 A1 | 2/2020 | Mironov et al. |
| 2021/0008788 A1 | 1/2021 | Murphy et al. |

OTHER PUBLICATIONS

Matai et al, "Progress in 3D bioprinting technology for tissue/organ regenerative engineering", Biomaterials, vol. 226, 32 pages, Oct. 2, 2019.

Extended European Search Report in EP application No. 21178593.6-1017, 16 pages, dated Oct. 21, 2021.

* cited by examiner

MODULAR PRINT BED FOR 3D BIOPRINTER

CROSS REFERENCE TO RELATED APPLICATIONS

The present disclosure claims priority to and the benefit of U.S. Provisional Application No. 63/036,546, filed on Jun. 9, 2020, entitled "MODULAR PRINT BED FOR 3D BIOPRINTER," which is herein incorporated by reference in its entirety for all purposes.

TECHNICAL FIELD

The present disclosure is generally directed towards the field of bioprinting, and more particularly, a modular print bed for a three-dimensional (3D) bioprinter.

BACKGROUND 3D bioprinting technologies allow for the fast fabrication of complicated biological structures for use in both scientific research and clinical applications. For example, 3D bioprinting may allow for the printing and patterning of cells into specific geometries in connection with drug screening, organ replacement, and the like.

Bioprinters are capable of printing complex multicellular geometrical constructs that allow scientists, researchers, and clinicians to study how cells are arranged within complex tissues and organs, and to perform physiological studies of organs. Bioprinters may be used to print and/or pattern single or multiple types of cells into different geometrical arrangements and three-dimensional structures such as tissues. Structures printed by bioprinters may be deposited onto print beds. However, print beds must be positioned and configured such that the receiving surface does not move with respect to the extruder, despite the vibrations that are associated with printing. Additionally, conventional print beds are incapable of being easily interchanged. For example, conventional print beds provide a single receiving surface that cannot be altered or exchanged.

Conventional print beds are configured to accommodate specific standardized laboratory vessel shapes. In this way, conventional bioprinters are limited by the shape of the vessel on the pre-installed print bed. Further, as print beds may have different functionalities (e.g., heating, cooling), conventional bioprinters may be limited by the functionality of the pre-installed print bed. Additionally in conventional systems, the specific laboratory vessel shapes may lead to poor retention of the receiving surface and poor heat distribution among any heated print beds Without the ability to switch bed plates, the functionality of the bioprinter in conventional systems is limited to the that what was initially designed with the bioprinter.

SUMMARY

The present disclosure is directed towards a 3D bioprinter having a modular, swappable print bed. In some embodiments, the modular, swappable print bed allows for the functionality of the bioprinter to be altered from the original design. For example, in some embodiments, the print bed may be swapped with one having different functionalities. Functionalities include, for example and without limitation, heating, cooling, photocuring, and imaging. Additionally, in another example, in some embodiments, the print bed may be swapped with one having differently shaped receiving surfaces. For example, receiving surfaces may include, without limitation, petri dishes, glass slides, well plates, custom dishes, and microfluidic chambers. Embodiments built in accordance with the present disclosure may be configured to accommodate differing standardized or specialized laboratory vessel shapes. Accordingly, the disclosed systems are no longer limited by the shape of the vessel on the pre-installed print bed. Additionally, the disclosed systems allow for the use of different functionalities.

In some embodiments, the print bed may include a recessed area configured to receive a variable insert. The variable insert may be easily interchanged and may provide a variety of surfaces onto which biomaterials may be deposited. The variable insert may include one or more glass slides, well plates, petri dishes, cage incubators, standard dishes, and custom dishes. The print bed may also include nozzle calibration and dish height sensors. In some embodiments, the print bed may be easily interchanged. The disclosed variable insert may be configured to provide a receiving surface that does not move with respect to the extruder despite the vibrations associated with printing. For example, in some embodiments the bioprinter may include a reinforced gantry, and the bioprinter may be configured to provide optimized movement controls to accommodate for vibrations due to printing.

In some embodiments, a bioprinter may include one or more printer heads, each of the one or more printer heads comprising one or more cartridges for receiving and holding a composition comprising biomaterials, and an extruder configured to extrude biomaterials from the cartridge and a modular print bed having a recessed area configured to receive a variable insert, wherein the extruder extrudes materials from the cartridge onto at least a portion of the variable insert. Optionally, the variable insert may include one or more glass slides, well plates, petri dishes, cage incubators, standard dishes, and custom dishes. Optionally, the modular print bed may also include a nozzle calibrator, and a dish height sensor. In some embodiments, the modular print bed further includes a temperature control unit configured to maintain the temperature of the variable insert between about 4° C. to about 60° C. The print bed may include universal clamps configured to hold the variable insert in a fixed position. In some embodiments, the well plate has one of 6, 12, 24, 48, 96, 384, or 1536 wells. In some embodiments, the petri dish has a diameter between about 30 mm and 100 mm. In some embodiments the standard dish or the custom dish has a length of less than 13 cm and a width of less than 9 cm.

In some embodiments, the modular print bed may include a nozzle calibrator configured to measure the location of the nozzle in relation to the modular print bed. Optionally, the nozzle calibrator may include at least one of an optical sensor, a touch detector, and an image based sensor. The printer head may include at least one of a syringe pump extruder head, a pressure driver extruder head or inkjet printing head. In some embodiments, the bioprinter may also include an electromagnetic radiation (EMR) module that emits EMR at a wavelength of about 405 nm or higher, and the EMR module may be configured to cure the extruded biomaterial.

In some embodiments, a method for printing an object having biological components, may include the steps of attaching a print bed having a variable insert with a printing surface, determining a relative positioning between the printing surface and a nozzle of an extruder for a bioprinter, determining a printer command based on the determined relative positioning and extruding biomaterials from the extruder onto the printing surface based on the determined printer command.

Optionally, the method may include the step of maintaining the temperature of the printing surface between about 4° C. to about 60° C. In some embodiments, determining the relative positioning between the printing surface and the nozzle of the extruder for a bioprinter may include shining an optical beam and detecting the interference of the nozzle with the optical beam. In other embodiments, determining the relative positioning between the printing surface and the nozzle of the extruder for the bioprinter may include obtaining a plurality of images, and applying an image processing algorithm to the obtained images to determine the location of the nozzle of the extruder. In another embodiment, determining the relative positioning between the printing surface and nozzle of the extruder for the bioprinter may include measuring a change in one of resistance or capacitance across a surface that contacts the nozzle of the extruder.

In some embodiments, extruding the biomaterials from the extruder onto the printing surface may include either pneumatic, piston, piezo-electric, or thermal extrusion. The method may also include the step of curing the extruded biomaterials by applying an electromagnetic radiation (EMR). In some embodiments, the EMR may have a wavelength at or above 405 nm.

DETAILED DESCRIPTION

The present disclosure includes a bioprinter having a modular print bed that includes a recessed area configured to receive a variable insert, a printer head having a cartridge for receiving and holding a biomaterial, and an extruder that is configured to extrude biomaterials from the cartridge onto a portion of the variable insert. The variable insert may be easily interchanged and may provide a variety of surfaces onto which biomaterials may be deposited. The variable insert may include one or more glass slides, well plates, petri dishes, cage incubators, standard dishes, and custom dishes. The modular print bed may also include various functionalities such as heating, cooling, and photocuring elements.

Figure 1A:
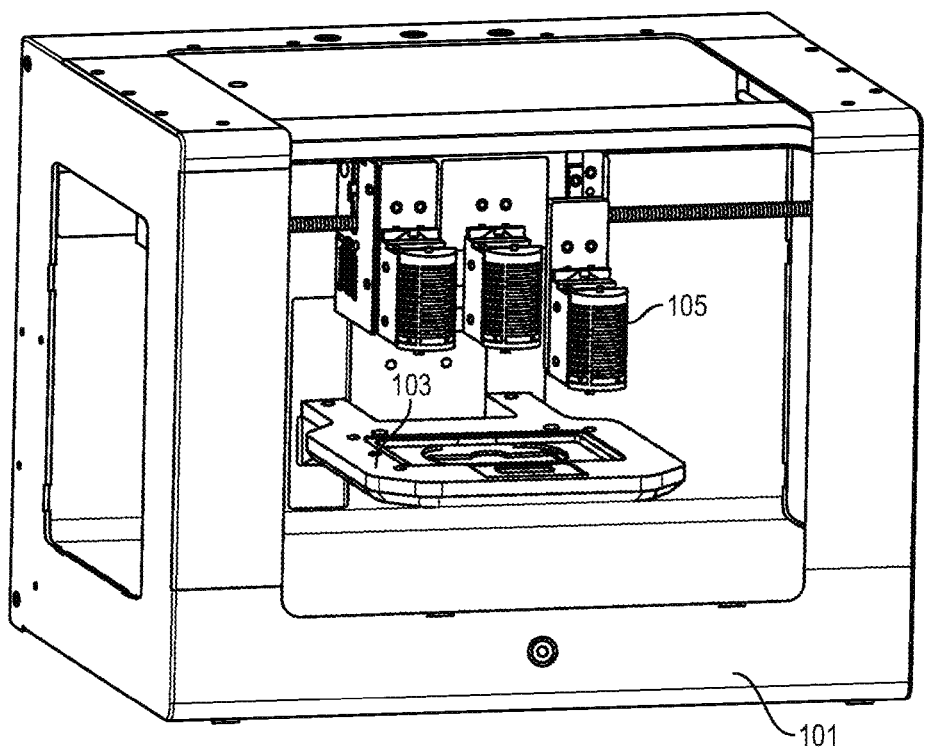
FIG. 1A illustrates a three-dimensional (3D) bioprinting system in a first perspective view in accordance with some embodiments of the present disclosure.
Figure 1B:
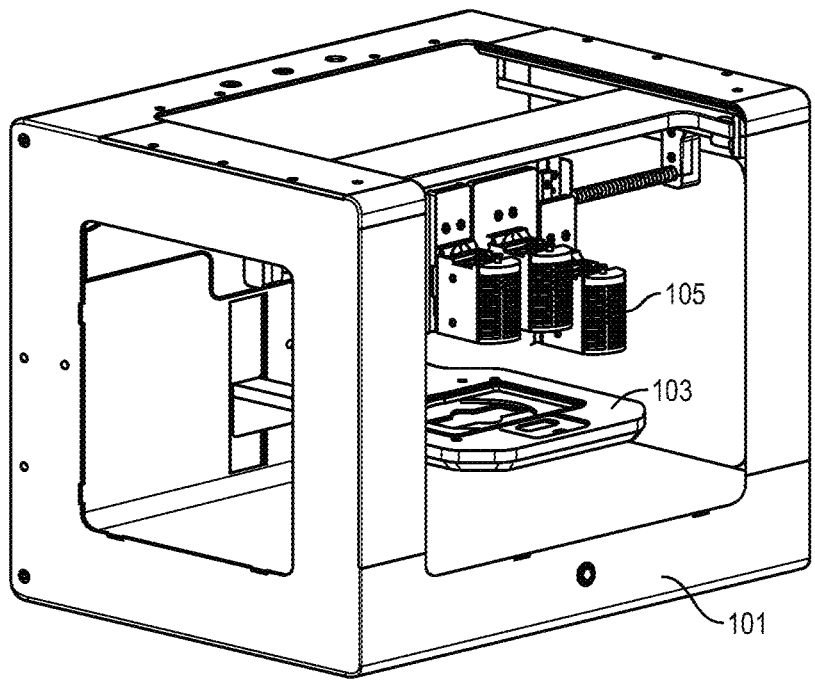
FIG. 1B illustrates the three-dimensional (3D) bioprinting system of FIG. 1A in a second perspective view in accordance with some embodiments of the present disclosure.

Disclosed herein is a three-dimensional (3D) bioprinting system with a modular print bed configured for a variable insert. FIG. 1A provides a first perspective view of a 3D bioprinting system. FIG. 1B provides a second perspective view of the 3D bioprinting system in FIG. 1A. As illustrated in FIGS. 1A and 1B, in some embodiments, the 3D bioprinting system includes a bioprinter 101 having a 3-axis system and a bed plate 103. The bed plate 103 may be configured to receive materials that are extruded through a cartridge-extruder assembly 105 of the 3D bioprinter 101. The bed plate 103 may be configured to hold a dish or other surface, onto which 3D structures may be deposited on via extrusion through a cartridge.

Cartridge-extruder assemblies 105 may be configured to extrude the materials, biomaterials, and hydrogels of interest from the cartridge onto the bed plate 103. The cartridge-extruders 105 may deposit the materials through either pneumatic, piston, piezo-electric, and thermal extrusion. In some embodiments, the bed plate 103 may be configured to translate across a single axis (e.g., z-axis). In some embodiments, the printer head includes at least one of a syringe pump extruder head, a pressure driver extruder head, or an ink jet printing head. As will be discussed below, in some embodiments, the bed plate 103 may be a modular bed plate such as modular bed plate 201 illustrated in FIG. 2.

In some embodiments, the three-dimensional bioprinter 101 may be used to fabricate cellular constructs such as tissues and organs using electromagnetic radiation (EMR) at or above 405 nm. The bioprinter 101 may include a material deposition device including a cartridge for receiving and holding a composition which contains biomaterial that cures after exposure to EMR. In some embodiments, the bioprinter 101 also includes an EMR module that emits EMR at a wavelength of about 405 nm or higher. In some embodiments the cartridge-extruder assemblies may each contains cells and/or other materials curable at a wavelength of about 405 nm or greater. The cells present in a chamber of the cartridge-extruder assembly 105 may be extruded through an orifice to form a cellular construct. In some embodiments, the EMR module may be integrated with a cartridge-extruder assembly 105 or adjacent to the cartridge-extruder assembly 105.

The bioprinter 101 may include one or more rods housed within the interior. In one embodiment, the rods may be placed at any direction or height and be of any width that is necessary to support one or more components of the bioprinter. In a further embodiment, the rods are placed along the x-axis, y-axis, or z-axis, or any combination thereof in the bioprinter. In another embodiment, the cartridge-extruder assemblies 105, receiving element such as bed plate 103, printer stage, or any combination thereof is attached to one or more rod. In a further embodiment, the cartridge-extruder assemblies 105 may move along one or more rods in the x- and y-directions and the printer stage moves along a rod in a z-direction. The rods may permit the receiving element or bed plate 103 to remain at the height needed to fabricate the article. The rods may also be utilized to calibrate and/or level one or more component of the bioprinter. In one embodiment, the rods control movement of one or more component of the bioprinter including, without limitation, the cartridge-extruder assemblies 105, printer stage, or any combination thereof. The movement of the rods may be performed using, without limitation, a motor.

Figure 2:
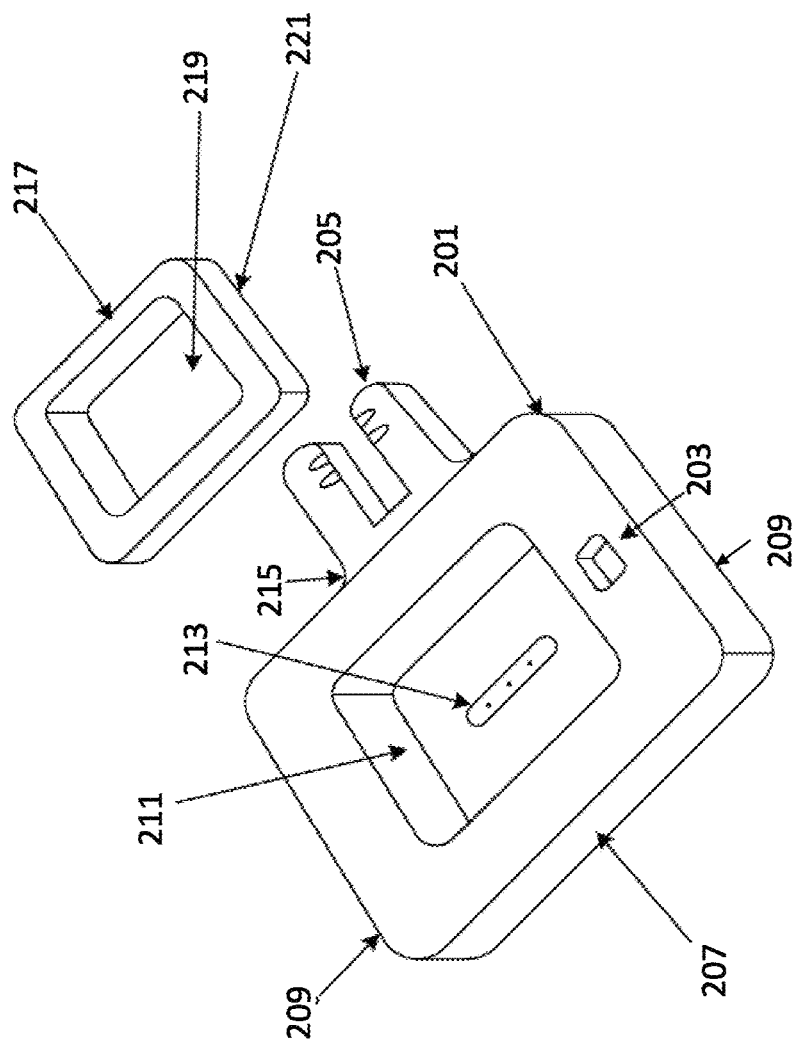
FIG. 2 illustrates a modular print bed in accordance with some embodiments of the present disclosure.

FIG. 2 illustrates a modular bed plate 201 for a 3D bioprinter such as bed plate 103 of FIGS. 1A and 1B. The bed plate 201 may have a front end 207, spaced apart from a back end 205 and two sides 209. The back end 205 may include a detachment and attachment mechanism 215. The detachment and attachment mechanism 215 may be configured to attach and/or detach the modular bed plate 201 from the bioprinter such as bioprinter 101. The modular bed plate

201 may include a nozzle auto calibration sensor 203, a base 211 which has a recessed area or space sized and/or configured to accommodate a variable insert 217. In some embodiments, the modular bed plate 201 may also include a dish height sensor.

The nozzle auto calibration sensor 203 may be configured to calibrate the position of the bed plate 201 with respect to a tip attached to the cartridge-extruder assembly of the bioprinter. In some embodiments, the nozzle auto calibration sensor 203 may detect the position of the extruder or cartridge tip (in the x, y, z position). The nozzle auto calibration sensor 203 may include mechanical, electrical, and/or laser parts. In some embodiments, the nozzle auto calibration sensor 203 includes one or more electrical pads. In some embodiments, the nozzle auto calibration sensor 203 in the modular bed plate 201 includes a mechanical switch or an optical sensor.

In some embodiments, the nozzle auto calibration sensor 203 may be configured to use a touch screen to detect the location of a nozzle tip. In such an embodiment, the modular bed plate 201 including the touch screen may be slowly moved along the Z-axis towards the extruder portion of the bioprinter 101 until contact is made between the touch screen and the nozzle. The relative resistances in the X and Y axis of the touch screen may be measured to determine the X and Y positions of nozzle. The touch screen may detect the location of the nozzle tip by measuring changes in resistance. For example, layers of the touch screen may cause changes in the resistance of the screen when they are pressed together as a result of contact with the nozzle. The touch screen may include electrodes positioned along the edges of the touch screen such that a voltage potential can be applied to opposing edges of the screen and the voltage drop across the screen may be measured by the two remaining edges thereby measuring the resistance of the screen in one of its axis. The process may be repeated by switching the axis.

Alternatively, in some embodiments, the nozzle auto calibration sensor 203 may include a one or more optical sensors configured to be triggered when a nozzle on the cartridge-extruder assembly of the bioprinter breaks a beam of light. In some embodiments, the nozzle auto calibration sensor 203 may include two optical beam sensors, each of which is configured to shine light across the X-axis and Y-axis, respectively. Or alternatively, in an embodiment where the nozzle auto calibration sensor 203 includes a singular sensor, the sensors may be positioned along a 45 degree in the X-Y plane.

In some embodiments, the nozzle of the extruder may be moved in a circular pattern in the X-Y plane while the bedplate may move vertically in the Z-direction. The nozzle may be moved at a speed such that the nozzle may complete one full circle in the X-Y plane in less than the time necessary for the nozzle to reach the bottom of the sensor well. Once an optical beam has been interfered with, the bedplate movement may be stopped and the nozzle may move in an x-sweep. The intensity of the light obfuscation can be a measured by the sensor and the X center location can be calculated based on a curve fit line to the sensor measurements. Then the sweep and center calculation may be repeated for the y axis. Once X and Y locations are calculated, the bedplate may move a small amount in the x-axis and a routine may be run to find the center position again. The process may produce two points each corresponding to X and Y coordinates of the center of the nozzle at two separate vertical locations along the Z-axis. The printer may then move in all three axes following the vector that passes though those two points until the sensor detects the end of the nozzle tip. When the sensor detects the end of the nozzle tip, the X and Y sweep may be performed again in order to refine the X and Y locations.

In some embodiments, an optical sensor of the nozzle auto calibration sensor 203 may include an infra-red beam that is produced by a light emitting diode (LED) or the like. The optical sensor may include a photodiode or phototransistor placed across a gap in front of the LED. Any object that interferes with the beam, may cause the photodiode or photo transistor and accompanying amplification to measure the reduced light. In some embodiments, where the beam coming from the LED and the receiving angle of the photodiode or phototransistor are greater than zero, partial obfuscation of the light beam may be measured. When the object obscuring the beam is within the relative size of the beam, as syringes and nozzle tips are, this partial beam measurement should produce a parabolic reading. The parabolic reading may be mathematically fitted and used to compute the exact center of the object.

In another alternative, in some embodiments, the nozzle auto calibration sensor 203 may be configured to automatically detect and calculate the center of the nozzle by analyzing an image from a camera. In such an embodiment, the nozzle auto calibration sensor 203 may include a camera that is configured to have a shallow field of focus and configured to take continuous images as the bedplate moves slowly along the Z-axis. The image taken by the camera of the nozzle auto calibration sensor 203 may undergo image processing techniques configured to recognize the position of the circular nozzle within the images taken based on contrast image analysis techniques applied to determine when and where the nozzle of the extruder entered the camera's field of focus.

In accordance with any of the described embodiments of the nozzle auto calibration sensor 203, the nozzle auto calibration sensor may be further configured to determine the relative location of the nozzle in an extruder with respect to the variable insert. Printer commands and print position may be based on the determined relative location of the nozzle in the extruder with respect to the variable insert. The information may be stored within the printer and the calculated offset in each of the three translation axes may be added to origin of the print location. In some embodiments, the auto calibration may be performed by the nozzle auto-calibration sensor 203 prior to each print unless a user specifies otherwise. The auto-calibration will also be available to a user anytime the print is paused or if the printer is not printing.

In some embodiments, the bed plate 201 may be configured to regulate the movement of a receiving device (such as a variable insert) that is configured to receive the 3D printed construct. The bed plate 201 may be configured to move the receiving device or variable insert along the z-axis. The bed plate 201 may be composed of glass, coated glass, plastic, coated plastic, metal, a metal alloy, gel, or any combination thereof. The bed plate 201 may be of any suitable shape such as substantially square, circular, triangular, oval, rectangular, or irregularly shaped. In some embodiments, the bed plate may have one or more cut outs or recessed areas configured to hold a receiving device such as petri dishes and/or well plates. The bed plate may have one or more recessed areas configured to hold functional elements such as heating and/or cooling elements.

In some embodiments, the bed plate 201 may be substantially rectangular in shape with a front end 207, spaced apart from a back end 205 and two sides 209. In some embodiments, a back end 205 of the bed plate may be attached to the bioprinter. In some embodiments the print bed plate 201 may be a modular add-in to the bioprinter that is fully detachable. In some embodiments, the print bed plate 201 may be integrated into the bioprinter.

The back end 205 may include a detachment and attachment mechanism 215. In some embodiments, the detachment and attachment mechanism 215 allows for the modular bed plate 201 to be interchangeable. In some embodiments, the detachment and attachment mechanism 215 includes a connector piece that is configured to slideably engage with a component bioprinter. In some embodiments, the back end 205 may be configured to attach to a bioprinter using screws, or other fastening elements. In some embodiments the detachment and attachment mechanism 215 may include screws configured to mount and mate to the bioprinter system. The front end 207 is configured to face the exterior of the bioprinter. For example the detachment and attachment mechanisms 215 may attach the modular bed plate 201 to a rod of the bioprinter.

In some embodiments, the bed plate has a substantially hollow interior area or base 211 that is configured to receive a variable insert 217. The base 211 can receive different types of inserts 217. In some embodiments one or more portions of the base 211 may include locking pins to align and attach the base 211 to the variable insert 217. In some embodiments, the variable insert 217 is only removed once there is no longer an extruded object or print located on top of it. Additionally, in some embodiments, the base 211 may have one or more electrical connectors 213 that are configured to communicate and/or power the variable insert 217.

In some embodiments the base 211 may be configured to provide power from the main power bus of the bioprinter (e.g. 24 volts, direct current). The base 211 may be further configured to have a digital communication connection to the modular bed plate (e.g., Universal Asynchronous Receiver/Transmitter (UART), Serial Peripheral Interface (SPI) or controller area network (CAN)) and several digital signals and analog signals configured to communicate with the sensor in the modular bedplate.

In some embodiments, the variable insert 217 may be configured to include a recessed area or space 219 configured to receive one or more of receiving devices such as dishes, glass slides, cage incubators, custom dish setups, and/or functional elements such as heating elements, and cooling elements. For example, in some embodiments, the space may be configured to hold six by thirty-five (6×35) mm dishes, four glass slides, and the like. In some embodiments, the variable inserts 217 form the bases onto which dishes are placed. The recessed area may be configured to have the dimension of the dish of interest.

In some embodiments, the modular bed plate 201 can include a recessed area or space 219 sized and/or configured to accommodate a variable insert 217. The recessed area or space 219 secures the variable insert 217 on the bed plate so that the variable insert 217 does not slide or otherwise move on the bed plate while any of the bioprinter components move in an x, y, or z direction.

In some embodiments, the variable insert 217 may be configured to hold well plates, petri dishes, glass slides, standard dishes, or custom dishes. In some embodiments, the well plates may include 6, 12, 24, 48, 96, 384, or 1536 wells. In some embodiments, the well plate may include any number of wells. Example of established multi-well plate formats include those found on 96-well plates (12×8 array of wells), 384-well plates (24×16 array of wells) and 1536-well plate (48×32 array of well). In some embodiments, the petri dishes may have a diameter between about 30 and 100 mm.

In some embodiments, the standard or custom dishes may have dimensions up to 13 cm in length and 9 cm in width. Additionally, in some embodiments the print bed may contain swappable inserts for 6×35 mm dishes, a plurality of glass slides (e.g., 4 glass slides), cage incubators, and custom dish setups. The print bed may also be configured to receive microfluidic chambers.

In some embodiments, the variable insert 217 may include heating and/or cooling elements and can be configured to maintain steady temperatures. For example, the print bed may be configured to cool to about 4° C. In another example, the print bed may be configured to heat to about 60° C. The variable insert 217 may include a temperature control unit having a source to heat or cool using thermal heating, thermo electric cooling, liquid heating, liquid cooling, electrical heating and the like. The temperature control unit may include heating and/or cooling pads. In this manner the print bed temperature may be used to control the temperature of the construct being created/printed on the print bed. In some embodiments, the temperature may be maintained by sensing the print bed's temperature and comparing it to the user's set temperature. The heating or cooling may be activated if the actual temperature deviates from the set temperature.

In some embodiments, the variable insert 217 may include photocuring elements. In some embodiments, the variable insert 217 may include imaging elements.

In some embodiments, the variable insert 217 may include a space for 221 for receiving petri dishes and plates and may include both locating and locking features. Locating features may be configured to hold the well plate or the petri dish in a fixed location without over constraining its location. The locating feature may have each of its three axis of translation and rotation constrained by one feature.

Figure 4:
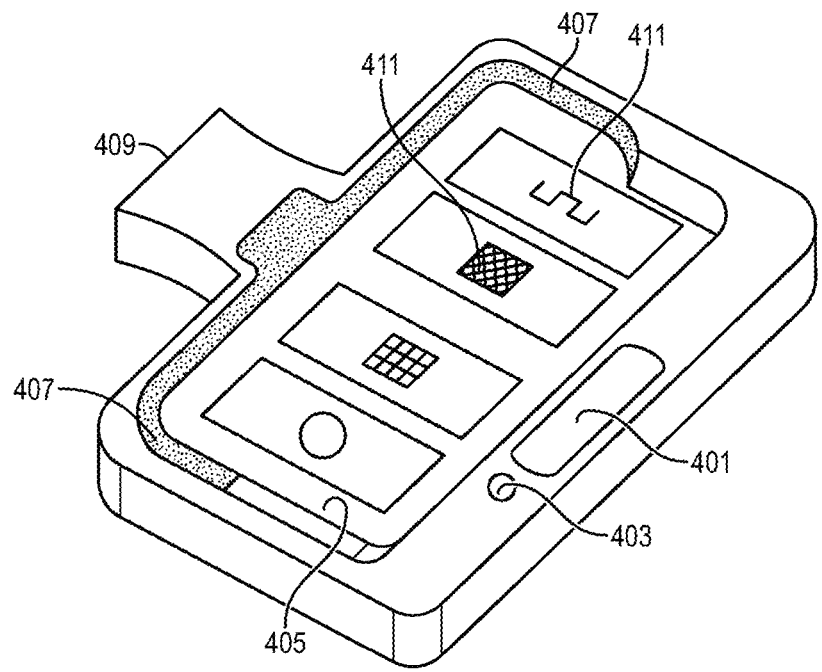
FIG. 4 illustrates a bed plate with glass slide insert in accordance with some embodiments of the present disclosure.
Figure 5:
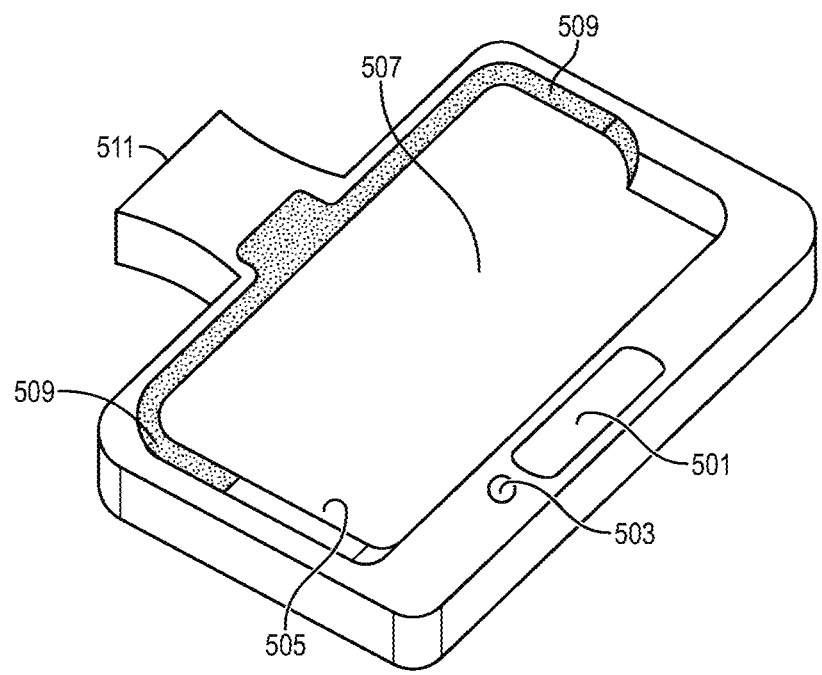
FIG. 5 illustrates a clamping system compatible with a modular print bed in accordance with some embodiments of the present disclosure.

In some embodiments, the variable insert 217 and/or the modular bed plate 201 may also include a dish height sensor (illustrated in FIGS. 4 and 5). In some embodiments, the dish calibration sensor may provide an indication of the dish height for the dish that is engaged in the variable insert 217 and/or modular bed plate 201. As all dishes have varying dish heights, the dish height sensor determines the dish height so that the distance of the nozzle to the printing surface can be determined. The distance of the nozzle to the printing surface may require both of the nozzle length and the dish height.

Figure 3:
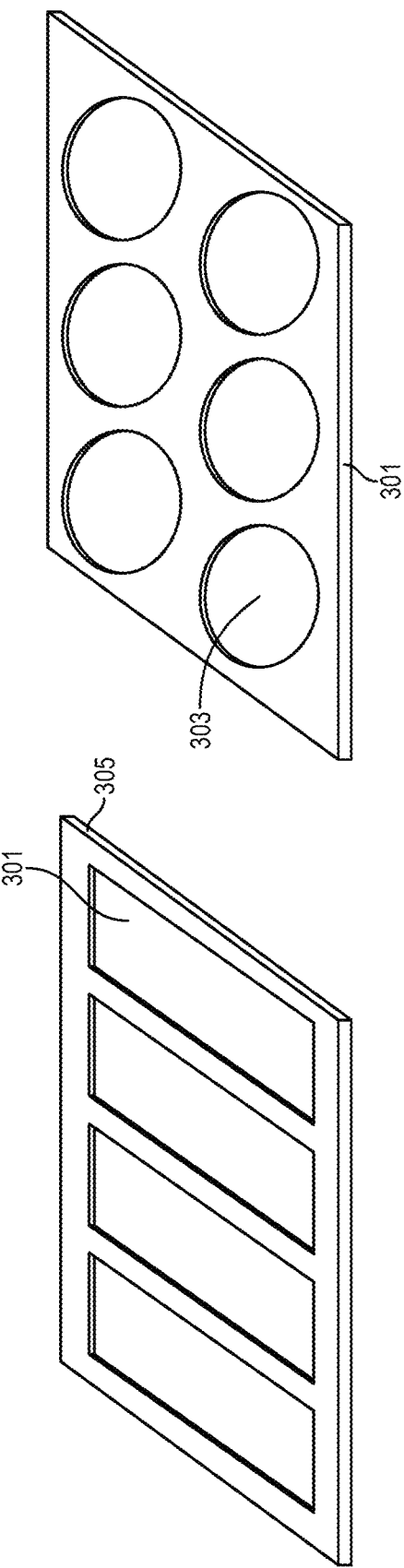
FIG. 3A illustrates a first bed plate insert in accordance with some embodiments of the present disclosure.
FIG. 3B illustrates a second bed plate insert in accordance with some embodiments of the present disclosure.

Examples of variable bed plate inserts, analogous to variable insert 217 of FIG. 2, are illustrated in FIGS. 3A and 3B. FIG. 3A illustrates a variable insert configured to hold glass slides. As depicted, in some embodiments, the variable bed plate insert may be configured to hold one or more glass slides 301. FIG. 3B illustrates a variable insert configured to hold petri dishes. In some embodiments, the variable bed plate insert may be configured to hold one or more petri dishes having a diameter of approximately 35 mm. In some embodiments, the variable bed plate inserts may include a connector 305 configured to engage the bed plate insert to the base of the print bed plate. In some embodiments, the connector 305 may be a sprung pin contact connector that allows the mechanical action of inserting the modular bedplate to also provide an electrical connection. In some embodiments, the connector 305 may be positioned on top of a bedplate holder that is flat with locating features. In this manner, embodiments built in accordance with the present disclosure may allow for the swapping of inserts between prints, switching the type of plate or dish that the user is bioprinting into. Further, the functionality of the bed plate (e.g., heating or cooling) may also be swapped.

FIG. 4 provides an illustration of a modular bed plate with a glass slide insert and samples of bioprinted constructs presented thereon. As illustrated, the modular bedplate can include a nozzle auto-calibration screen 401, a dish calibration sensor 403, a variable insert including a plurality of glass slides 405, a universal clamping system 407, a connector 409 configured to engage the modular bed plate with the bioprinter. As depicted, bioprinted structures 411 may be deposited onto the glass slides.

In some embodiments, the nozzle auto-calibration screen 401 may be configured to sense contact with the auto-calibration screen 401 as a way to determine the position of an object that makes contact with the auto-calibration screen 401. In some embodiments, the universal clamping system 407 may be analogous to a microscope clamping system, and may include a spring tensioned arm that is configured to pull both revaluate well pates and circular petri dishes into contact with two edges. Dish calibration sensor 403 may provide an indication of the dish height for the dish that is engaged in the variable insert and/or modular bed plate.

FIG. 5 provides an illustration of a modular bed plate with universal clamping system. The modular bed plate includes a nozzle auto-calibration screen 501, a dish calibration sensor 503, a well plate base 505 including a space configured to receive inserts and/or well plates 507, a universal clamping system 509, and a connector 511. Inserts and/or well plates may be positioned within the space 507. Example inserts and/or well plates include 6×35 mm dishes, glass slides, cage incubators, custom dish setups and the like. In some embodiments, a plurality of glass slides may be positioned within the space 507.

In some embodiments, the universal clamping system 509 may be configured to hold well plates of different sizes (e.g., 6, 12, 24, 48, 96, 384, and 1536 wells), petri dishes of various diameters (e.g., 30-100 mm diameter), glass slides, or standard and/or custom dishes with dimensions up to 13 cm in length and 9 cm in width.

Methods in accordance with the present disclosure may include a method for printing an object having biological components. Such methods may include the steps of providing a print bed having a variable insert on a printing surface, determining a relative positioning between the printing surface and a nozzle of an extruder for a bioprinter, determining a printer command based on the determined relative positioning, and extruding biomaterials from the extruder onto the printing surface based on the determined printer command. For example, determining the relative positioning may include determining a dish height by a dish height sensor and determining a nozzle position by a nozzle auto calibration sensor. Each sensor may provide x,y,z coordinates for the printing service. Additionally, determining a printer command may include determining coordinates that are then used to calculate nozzle extrusion parameters for the specified printing distance. The determined coordinates may be used as the origin point for a bioprinting file.

While illustrative embodiments have been described herein, the scope thereof includes any and all embodiments having equivalent elements, modifications, omissions, combinations (e.g., of aspects across various embodiments), adaptations and/or alterations as would be appreciated by those in the art based on the present disclosure. For example, the number and orientation of components shown in the exemplary systems may be modified. Further, with respect to the exemplary methods illustrated in the attached drawings, the order and sequence of steps may be modified, and steps may be added or deleted. Thus, the foregoing description has been presented for purposes of illustration. It is not exhaustive and is not limiting to the precise forms or embodiments disclosed.

We claim:

1. A bioprinter comprising:
a modular print bed comprising:
a front end;
a back end opposite the front end, the back end comprising a connector assembly configured to connect the modular print bed with the bioprinter; and
a top side extending between the front end and the back end, the top side comprising a first recessed area configured to receive a variable insert such that the variable insert does not move relative to the modular print bed, the first recessed area comprising one or more electrical connectors configured to power the variable insert, the variable insert comprising a second recessed area configured to receive a receiving device, the variable insert comprising a temperature control unit configured to maintain the temperature of the variable insert between about 4° C. to about 60° C.,
wherein the modular print bed is movable relative to an extruder of the bioprinter; and
a printer head positioned above the modular print bed, the printer head comprising:
a cartridge for receiving and holding a biomaterial, and
the extruder configured to extrude biomaterials from the cartridge onto a portion of the receiving device.

2. The bioprinter of claim 1, wherein the receiving device comprises one or more glass slides, well plates, petri dishes, cage incubators, standard dishes, and custom dishes.

3. The bioprinter of claim 1, wherein the modular print bed further comprises a nozzle calibrator configured to measure the location of the nozzle in relation to the modular print bed.

4. The bioprinter of claim 3, wherein the nozzle calibrator further comprises at least one of an optical sensor, a touch detector, and an image based sensor.

5. The bioprinter of claim 1, wherein the modular print bed further comprises a dish height sensor configured to measure at least one of a height or rotation of a printing surface with respect to a position of the variable insert.

6. The bioprinter of claim 1, wherein the temperature control unit is configured to use thermal heating, thermoelectric cooling, liquid heating, liquid cooling, or electrical heating.

7. The bioprinter of claim 1, wherein the modular print bed further comprises universal clamps configured to hold the variable insert in a fixed position.

8. The bioprinter of claim 2, wherein the well plate has one of 6, 12, 24, 48, 96, 384, or 1536 wells.

9. The bioprinter of claim 2, wherein the petri dish has a diameter between about 30 mm and 100 mm.

10. The bioprinter of claim 2, wherein the standard dish or the custom dish has a length of less than 13 cm and a width of less than 9 cm.

11. The bioprinter of claim 1, wherein the printer head comprises at least one of a syringe pump extruder head, a pressure driver extruder head or ink jet printing head.

12. The bioprinter of claim 1, further comprising an electromagnetic radiation (EMR) module that emits EMR at a wavelength of about 405 nm or higher, wherein the EMR module is configured to cure the extruded biomaterial.

* * * * *